(12) United States Patent
Harper et al.

(10) Patent No.: US 9,513,155 B2
(45) Date of Patent: Dec. 6, 2016

(54) APPARATUS AND METHOD FOR VOLUME AND MASS ESTIMATION OF A MULTIPHASE FLUID STORED AT CRYOGENIC TEMPERATURES

(71) Applicant: Westport Power Inc., Vancouver (CA)

(72) Inventors: Gregory C. Harper, Delta (CA); Gregory A. Batenburg, Delta (CA); Paul S. Schranz, Bowen Island (CA)

(73) Assignee: WESTPORT POWER INC., Vancouver (CA)

( * ) Notice: Subject to any disclaimer, the term of this patent is extended or adjusted under 35 U.S.C. 154(b) by 266 days.

(21) Appl. No.: 14/226,650

(22) Filed: Mar. 26, 2014

(65) Prior Publication Data

US 2014/0223992 A1 Aug. 14, 2014
US 2016/0054170 A9 Feb. 25, 2016

Related U.S. Application Data

(63) Continuation of application No. PCT/CA2012/050628, filed on Sep. 11, 2012.

(30) Foreign Application Priority Data

Sep. 27, 2011 (CA) .................................... 2753588

(51) Int. Cl.
*G01N 7/00* (2006.01)
*G01F 25/00* (2006.01)
(Continued)

(52) U.S. Cl.
CPC ......... *G01F 25/0084* (2013.01); *F17C 13/021* (2013.01); *G01F 23/0061* (2013.01);
(Continued)

(58) Field of Classification Search
CPC G01M 15/102; G01F 23/263; G01F 23/268; G01F 23/266; G01F 25/0084; G01N 15/0656

USPC .............. 73/23.31, 29.03, 24.01, 304 C, 311
See application file for complete search history.

(56) References Cited

U.S. PATENT DOCUMENTS 3,797,311 A 3/1974 Blanchard et al.
4,594,892 A * 6/1986 Asmundsson ........ G01F 23/268
210/416.4
(Continued)

FOREIGN PATENT DOCUMENTS

CA 2626960 A 9/2008
CN 101038201 A 9/2007
(Continued)

OTHER PUBLICATIONS

Office Action issued by the State Intellectual Property Office of the People's Republic of China on Feb. 28, 2015, in connection with Chinese Patent Application No. 201280047366.3.
(Continued)

*Primary Examiner* — Eric S McCall
*Assistant Examiner* — Mohammed E Keramet-Amircolai
(74) *Attorney, Agent, or Firm* — Carie Mager; C. L. Kyle (57) ABSTRACT

An apparatus and method estimate fluid mass in a cryogenic tank that holds a multiphase fluid comprising a liquid and a vapor. The apparatus comprises a level sensor, a pressure sensor and a computer. The level sensor provides a parameter representative of a level of the liquid. The pressure sensor provides a pressure signal representative of vapor pressure inside the cryogenic tank. The computer is operatively connected with the level sensor and the pressure sensor to receive the parameter and the pressure signal, and is programmed to determine the level from inputs comprising the parameter, to calculate a first volume of the liquid from inputs comprising the level, and to calculate a first mass of the liquid from inputs comprising the first volume and the pressure signal.

43 Claims, 5 Drawing Sheets

(51) Int. Cl.
| | |
|---|---|
| *G01F 23/30* | (2006.01) |
| *G01F 23/14* | (2006.01) |
| *G01F 23/26* | (2006.01) |
| *G01F 23/296* | (2006.01) |
| *G01F 23/00* | (2006.01) |
| *F17C 13/02* | (2006.01) |
| *G01N 9/24* | (2006.01) |
| *G01F 17/00* | (2006.01) |

(52) U.S. Cl.
CPC ........... *G01F23/14* (2013.01); *G01F 23/26* (2013.01); *G01F 23/296* (2013.01); *G01F 23/30* (2013.01); *G01F 25/00* (2013.01); *F17C 2201/0109* (2013.01); *F17C 2201/035* (2013.01); *F17C 2201/056* (2013.01); *F17C 2201/058* (2013.01); *F17C 2203/0629* (2013.01); *F17C 2205/0332* (2013.01); *F17C 2221/011* (2013.01); *F17C 2221/012* (2013.01); *F17C 2221/014* (2013.01); *F17C 2221/016* (2013.01); *F17C 2221/033* (2013.01); *F17C 2223/0161* (2013.01); *F17C 2223/033* (2013.01); *F17C 2223/047* (2013.01); *F17C 2225/045* (2013.01); *F17C 2250/032* (2013.01); *F17C 2250/043* (2013.01); *F17C 2250/0417* (2013.01); *F17C 2250/0421* (2013.01); *F17C 2250/0473* (2013.01); *F17C 2250/0495* (2013.01); *F17C 2260/025* (2013.01); *F17C 2260/026* (2013.01); *F17C 2270/0168* (2013.01); *G01F 17/00* (2013.01); *G01N 9/24* (2013.01); *Y02E 60/321* (2013.01)

(56) References Cited

U.S. PATENT DOCUMENTS

| | | | |
|---|---|---|---|
| 4,716,536 A | 12/1987 | Blanchard | |
| 5,018,387 A | 5/1991 | Myneni | |
| 5,103,368 A | 4/1992 | Hart | |
| 5,195,058 A * | 3/1993 | Simon | G01F 23/2962 340/621 |
| 5,553,479 A | 9/1996 | Rauchwerger | |
| 5,635,621 A | 6/1997 | Lawson | |
| 5,651,473 A | 7/1997 | Preston et al. | |
| 5,743,136 A * | 4/1998 | Gaston | G01F 23/36 73/308 |
| 6,016,697 A * | 1/2000 | McCulloch | G01F 23/266 73/304 C |
| 6,529,017 B2 | 3/2003 | Martin et al. | |
| 6,539,797 B2 | 4/2003 | Livingston et al. | |
| 6,857,313 B2 | 2/2005 | Williamson | |
| 6,892,572 B2 | 5/2005 | Breed et al. | |
| 7,284,427 B2 | 10/2007 | Calabrese | |
| 7,461,550 B2 | 12/2008 | Calabrese | |
| 7,555,916 B2 | 7/2009 | Dickerson et al. | |
| 7,665,358 B2 | 2/2010 | Calabrese | |
| 7,711,509 B2 | 5/2010 | Woodard et al. | |
| 7,784,342 B2 | 8/2010 | Johnson et al. | |
| 2002/0157402 A1 | 10/2002 | Drube et al. | |
| 2004/0079150 A1* | 4/2004 | Breed | B60J 10/00 73/291 |
| 2005/0139600 A1* | 6/2005 | Harper | F17C 1/00 220/560.13 |
| 2006/0156809 A1 | 7/2006 | Immel | |
| 2008/0134693 A1* | 6/2008 | Harper | F17C 1/12 62/50.7 |
| 2008/0209915 A1* | 9/2008 | Harper | F17C 3/00 62/45.1 |
| 2008/0302111 A1* | 12/2008 | Batenburg | F04B 9/105 62/50.6 |
| 2009/0211267 A1 | 8/2009 | Kim et al. | |
| 2009/0301189 A1 | 12/2009 | Ross, Jr. et al. | |
| 2009/0301190 A1 | 12/2009 | Ross, Jr. et al. | |
| 2010/0005788 A1* | 1/2010 | McConnell | F01N 3/0253 60/286 |
| 2010/0132431 A1 | 6/2010 | Hernandez et al. | |
| 2010/0145638 A1 | 6/2010 | Begin | |
| 2011/0090088 A1* | 4/2011 | Kenney | G01F 23/68 340/623 |

FOREIGN PATENT DOCUMENTS

| | | |
|---|---|---|
| CN | 101287971 A | 10/2008 |
| EP | 2289729 A | 3/2011 |
| EP | 2339222 A2 | 6/2011 |
| FR | 2885217 A | 11/2006 |
| GB | 1384390 A | 2/1975 |
| JP | 2006160287 A | 6/2006 |
| WO | 8502445 A | 6/1985 |
| WO | 8505177 A | 11/1985 |
| WO | 0179789 A | 10/2001 |
| WO | 2008121661 A | 10/2008 |

OTHER PUBLICATIONS

International Preliminary Report on Patentability Issued by the International Bureau on Apr. 1, 2014 in connection with PCT/CA2012/050628.

International Search Report and Written Opinion of the International Searching Authority issued on Dec. 4, 2012, in connection with International Application No. PCT/CA2012/050628.

Office Action issued by the Canadian Intellectual Property Office on May 20, 2014 in connection with Canadian Application No. 2,753,588.

Search Report issued by SIPO on Jan. 12, 2016 in connection with co-pending Chinese Application No. 201280047366.3.

* cited by examiner

APPARATUS AND METHOD FOR VOLUME AND MASS ESTIMATION OF A MULTIPHASE FLUID STORED AT CRYOGENIC TEMPERATURES

CROSS-REFERENCE TO RELATED APPLICATIONS

This application is a continuation of International Application No. PCT/CA2012/050628 having an international filing date of Sep. 11, 2012 entitled "Apparatus And Method For Volume And Mass Estimation Of A Multiphase Fluid Stored At Cryogenic Temperatures". The '628 international application claimed priority benefits, in turn, from Canadian Patent Application No. 2,753,588 filed on Sep. 27, 2011. The '628 international application is hereby incorporated by reference herein in its entirety.

FIELD OF THE INVENTION

An apparatus and method estimate a volume and a mass of a multiphase fluid stored at cryogenic temperatures in a vessel. When the multiphase fluid is a fuel consumed by a vehicle, the apparatus and method can be used to estimate vehicle range.

BACKGROUND OF THE INVENTION

The employment of alternative fuels such as liquefied natural gas (LNG) to power automotive vehicles has provided advantages that are both economical and environmental compared to conventional hydrocarbon fuels such as gasoline and diesel. Accordingly there is a growing demand for vehicles that are fuelled exclusively by LNG, and for bi-fuel vehicles whose engines are capable of fuelling from gasoline or diesel in addition to LNG.

Gasoline and diesel are incompressible liquids and accordingly, unlike gaseous fuels their densities do not change as a function of pressure. The heating value of gasoline or diesel is substantially constant and orthogonal to pressure. A measurement of the volume of gasoline or diesel remaining in a fuel tank provides sufficient information to determine the energy content available to power a vehicle. This is not the case for LNG.

Measuring the volume of LNG provides a vehicle operator with information they can use to estimate when a trip to a refuelling station is necessary. However, the density of LNG is a function of temperature, pressure and fluid composition, and therefore the energy content in any given volume is variable. At the pressures and temperatures that LNG is typically stored, it is a multiphase fluid, and the density of the liquefied gas is variable as a function of the saturated pressure and temperature. A measure of the liquid volume in a fuel tank provides less accurate information to estimate the energy content available to power a vehicle, in comparison to gasoline or diesel. For example, under typical storage conditions the density of LNG in a cryogenic storage tank can vary up to 20% or more. The vapor pressure within a cryogenic storage tank changes due to boiling and natural expansion of the LNG as a result of heat leak into the cryogenic space from the external environment because of the finite thermal resistance of tank insulation. For a given mass of LNG, however, the energy content available to power a vehicle is the same even though its volume and density can vary by 20%. Therefore determining the mass of LNG provides a more accurate estimation of its energy content and therefore fuelling range of a vehicle.

It is known to use level sensors to measure a liquid level of LNG in a cryogenic storage tank. However, accurately measuring the liquid level of a cryogenic liquid held in a storage tank is still a challenging application. It can be especially challenging to accurately measure liquid level of cryogenic liquids in storage tanks that are mobile, such as vehicular fuel tanks storing LNG. There are known methods available for determining the liquid level of a cryogenic liquid held within a storage tank that employ level sensors. There are various types of level sensors including mechanical float-type level sensors, pressure-based level sensors, ultrasonic level sensors and capacitance-type level sensors. It is known to use a capacitance-type level sensor for measuring liquid levels inside a cryogenic storage tank.

The capacitance-type level sensor has proven to be particularly well suited for measuring the level of LNG in a storage tank. The evolution of capacitance-type level sensors has provided sensors of varying complexity and accuracy tailored to particular application requirements. The basic operating principle behind a capacitance-type level sensor is to arrange two conductors within a tank where the liquid level is to be measured. The conductors are electrically insulated by a space that provides for a dielectric material. That is, the LNG between the conductors in liquid or vapor form serves as the dielectric material. The combination of the conductors and the dielectric material therebetween provides a capacitor. A capacitance of the capacitor is directly proportional to the surface area of the conductors, the distance separating the conductors and an effective dielectric constant of the dielectric materials between them. As the level of liquid rises or falls within the tank, the effective dielectric constant of the dielectric between the conductors changes and so too does the capacitance. By detecting changes in the capacitance of the capacitor the level of the liquid in the tank can be determined.

For the purposes of this application, cryogenic fuels include those liquid fuels that boil at temperatures at or below $-100°$ C. under atmospheric pressures. For example, LNG boils at approximately $-162°$ C. at atmospheric pressure. While the present description pertains to LNG, it is equally as applicable to other multiphase fluids generally, for example methane, ethane, propane, hydrocarbon derivatives, hydrogen, nitrogen, argon and oxygen.

Accurately detecting the level of liquid remaining for vehicular fuel tank applications is important because the consequence of an inaccurate level measurement can result in a vehicle being stranded if it runs out of fuel, or reduced operational efficiency if the vehicle is re-fuelled more frequently than necessary. In addition, for vehicles that use a high pressure pump to deliver the fuel to the engine, there can be accelerated wear of the pump components if the pump is operated frequently when the fuel tank is empty.

During refuelling of a cryogenic storage tank an ullage space needs to be provided for natural expansion of vapors from boiling of the cryogenic liquid. One of the challenges of LNG is that, in many applications, once delivered into the storage tank, it needs extra space in which to expand when the LNG warms. Excessive heat leakage into a cryogenic tank, as well as causing the LNG itself to expand, will cause the cryogenic liquid to boil. Eventually, with continued heat leakage, LNG will boil or evaporate resulting in a pressure build up in the storage tank.

One problem with use of the ullage space is that it is difficult to leave an adequate space during filling. In other words, refuelling must be stopped at some predetermined point prior to the storage tank reaching liquid full. Ideally, the ullage space should be large enough to allow for LNG expansion yet small enough to maximize the amount of cryogen that can be held in the tank and, thereby, maximize the time between refuelling. As noted above, this is important in natural gas vehicle operations where fuel systems attempt to maximize the volume they can store within the limited space available on a vehicle while minimizing the space utilized to store that fuel. A variety of means have been developed to determine a fill point that leaves an adequate ullage space.

Visual fill lines, if used, may not provide the level of accuracy required. Also, given the double-walled, vacuum insulated structure of many tanks, it is not easy to provide a sight port through to the inner vessel. Stop mechanisms such as shut-off floats or valves require mechanical parts within the inner vessel. This introduces into the storage tank a mechanical failure point that is subjected to wear during and between each fill.

Level sensors have been used in cryogenic storage tanks. However, in order to calibrate the level sensor the storage tanks have traditionally required filling which is problematic for a number of reasons. First, it is difficult to achieve when an ullage space is required and no visual fill lines are present. Second, filling of a storage tank during manufacturing is not desired since the tank then needs to be emptied after calibration for shipping. Also, once the level sensor is assembled into the tank it is difficult to gain further access if required for calibration purposes.

U.S. Pat. No. 6,892,572 issued to Breed et al. on May 17, 2005 discloses a system for determining a quantity of a liquid in a fuel tank in a vehicle subject to varying external forces caused by movement or changes in the roll and pitch angles of the vehicle wherein the tank is mounted to the vehicle and subject to forces along the yaw axis of the vehicle. One or more tank load cells provide an output proportionally representing the load thereon. The load cells are placed between a portion of the tank and a portion of a reference surface of the vehicle and are sensitive along an axis that is substantially normal to the mounting surface and generally parallel to the yaw axis of the vehicle.

French Pat. No. 2,885,217, issued to Bruno Bernard on Aug. 10, 2007, discloses a gaseous fuel quantity measuring gauge for a fuel tank of a vehicle comprising sensors measuring pressure and temperature of fuel within the fuel tank. There is also disclosed a method and apparatus for estimating the mass of a liquid disposed below the gaseous fuel. Bernard teaches an arrangement, which employs multiple sensors that introduce further heat paths between the storage vessel and the outside environment, increasing the boiling rate of the liquid within the vessel. Furthermore, Bernard disclosed that the pressure sensor must be disposed at the bottom of the tank in an inconvenient location for mounting, thereby complicating the manufacturing of the storage vessel and introducing an additional failure point that either shortens the operational life of the fuel tank or increases the maintenance costs.

A fluid level sensor employing multiple stacked capacitive sensors is disclosed in U.S. Pat. No. 3,797,311 issued on Mar. 19, 1974 to Blanchard et al. The fluid sensor comprises a lower segment, an intermediate segment and an upper segment. When a level of fluid is within the range of the upper segment, the lower and intermediate segments do not contribute at all to the level measurement. Instead, a fixed height of the lower and intermediate segments measured before installation is added to the output of the upper segment.

A capacitive level sensor and control system is disclosed in U.S. Pat. No. 6,016,697, issued Jan. 25, 2000 to McCulloch et al. The capacitive level detection and control system provides a highly accurate determination of liquid level within a container. The primary sensor is an elongate capacitive probe positioned vertically within the container so that a lower portion of the probe is in liquid and an upper portion of the probe extends above the surface of the liquid. A liquid reference sensor is proximate the lower end of the probe, and a gas reference sensor is proximate the upper end of the probe. The gas reference sensor and the liquid reference sensor assist in calibration of the system and provide capacitances proportional to liquid and gas dielectric constants. The calibration requires that all three sensors be placed in the same medium, for example air, so that voltages can be measured. During operation, then, the level measurement is independent of the dielectric constant of the liquid whose level is being measured.

There is a need for a new and improved apparatus and method for determining the volume and mass of a multiphase fluid that employs a level sensor measurement.

SUMMARY OF THE INVENTION

An improved method estimates fluid mass in a cryogenic tank that holds a multiphase fluid comprising a liquid and a vapor. The method comprises steps of determining a level of the liquid in the cryogenic tank, calculating a first volume of the liquid from inputs comprising the level of the liquid, measuring vapor pressure inside the tank, and calculating a first mass of the liquid from inputs comprising the first volume and the vapor pressure. The method further comprises a step of estimating a fuelling range for a vehicle based on the first mass when the fluid is a fuel for combustion in an internal combustion engine in the vehicle. When the step of determining the level of the liquid employs a capacitance-type level sensor, the method comprises sub-steps of providing a pair of spaced apart conductors that are disposed within the cryogenic tank and form in part a capacitor; and calibrating the capacitance-type level sensor at least once prior to first introduction of the cryogenic liquid in the cryogenic tank. The step of calibrating comprises steps of applying a measuring signal to the capacitor; measuring a first parameter representative of a first capacitance of the capacitor in a dry state where a first dielectric with a first dielectric constant is disposed between the spaced apart conductors in the dry state; estimating a second parameter representative of an empty level in the cryogenic tank where a second dielectric with a second dielectric constant is disposed between the spaced apart conductors at the empty level and the second parameter is estimated based on the first parameter and a first ratio of dielectric constants comprising the first dielectric constant and the second dielectric constant; and estimating a third parameter representative of a full level in the cryogenic tank where a third dielectric with a third dielectric constant is disposed between the spaced apart conductors at the full level and the third parameter is estimated based on the first parameter and a second ratio of dielectric constants comprising the first dielectric constant and the third dielectric constant. The second dielectric is the vapor and the third dielectric is the liquid. The second dielectric constant and the third dielectric constant can be determined as a function of the vapor pressure. When employing the capacitance-type level sensor the step of determining the level comprises sub-steps of applying the measuring signal to the capacitor; measuring a fourth parameter representative of the level of the liquid in the cryogenic tank; and calculating the level from inputs comprising the second parameter, the third parameter, the empty level, the full level and the fourth parameter. The calculation can be done by interpolating the level between the empty level and the full level based on the fourth parameter. The first volume can be calculated by employing a mathematical relationship between the level and the first volume or an empirical relationship between the level and the first volume. The first mass can be calculated by estimating the density of the liquid from inputs comprising the vapor pressure and calculating the first mass from inputs comprising the density and the first volume. The density can be estimated by employing a mathematical relationship between the vapor pressure and the density, or by employing an empirical relationship between the vapor pressure and the density. For example, the density can be estimated from inputs comprising a speed of propagation of acoustic waves through the liquid, or the density can be estimated based on the composition of the liquid. When the liquid is natural gas the composition can be estimated based on the percentage composition of methane. The method can further comprise a step of calculating a second mass of the vapor where a total fluid mass is the sum of the first mass and the second mass. The total fluid mass can be employed to estimate fuelling range for a vehicle when the fluid is a fuel for combustion in an internal combustion engine of a vehicle. The second mass can be calculated based on steps comprising calculating a second volume occupied by the vapor, estimating a density of the vapor, and estimating the second mass based on the second volume and the density. The density of the vapor can be determined based on the vapor pressure and the vapor composition.

An improved apparatus is provided for estimating fluid mass in a cryogenic tank that holds a multiphase fluid comprising a liquid and a vapor. The apparatus comprises a level sensor, a pressure sensor and a computer. The level sensor provides a parameter representative of a level of the liquid. The pressure sensor provides a pressure signal representative of vapor pressure inside the cryogenic tank. The computer is operatively connected with the level sensor and the pressure sensor to receive the parameter and the pressure signal. The computer is programmed to determine the level from inputs comprising the parameter, to calculate a first volume of the liquid from inputs comprising the level, and to calculate a first mass of the liquid from inputs comprising the first volume and the pressure signal. When the fluid is a fuel for combustion in an internal combustion engine in a vehicle, the computer can be further programmed to estimate a fuelling range for the vehicle based on the first mass. The level sensor can be a float-type level sensor, an ultrasonic-type level sensor, a pressure-type level sensor or a capacitance-type level sensor. The capacitance-type level sensor comprises a pair of spaced apart conductors disposed within the cryogenic tank and a measurement apparatus that is operatively connected with the spaced apart conductors and is adapted to apply a measuring signal thereto and measure instantaneous values of parameters therefrom representative of corresponding instantaneous values of capacitance of the spaced apart conductors. The computer is in communication with the measurement apparatus and is further programmed to calibrate the capacitance-type level sensor at least once prior to first introduction of the cryogenic liquid in the cryogenic tank. The computer is programmed to command the measuring signal be applied to the spaced apart conductors, to receive a first parameter from the measurement apparatus representative of a first capacitance of the spaced apart conductors in a dry state where a first dielectric with a first dielectric constant is disposed between the spaced apart conductors, to estimate a second parameter representative of an empty level in the cryogenic tank where a second dielectric with a second dielectric constant is disposed between the spaced apart conductors at the empty level and the second parameter is estimated based on the first parameter and a first ratio of dielectric constants comprising the first dielectric constant and the second dielectric constant, and to estimate a third parameter representative of a full level in the cryogenic tank where a third dielectric with a third dielectric constant is disposed between the spaced apart conductors at the full level and the third parameter is estimated based on the first parameter and a second ratio of dielectric constants comprising the first dielectric constant and the third dielectric constant. The second dielectric is the vapor and the third dielectric is the liquid. The second dielectric constant and the third dielectric constant can be calculated based on the vapor pressure. The computer is further programmed to command the measuring signal be applied to the spaced apart conductors, to receive a fourth parameter from the measurement apparatus representative of the level of the liquid, and to calculate the level from inputs comprising the second parameter, the third parameter, the empty level, the full level and the fourth parameter. The computer can be further programmed to interpolate the level between the empty level and the full level based on the fourth parameter. The computer can be programmed to employ either a mathematical relationship between the level and the first volume, or an empirical relationship between the level and the first volume in order to calculate the first volume. The computer can be further programmed to estimate the density of the liquid from inputs comprising the vapor pressure, and to calculate the first mass from inputs comprising the density and the first volume. The computer can still be further programmed to employ either a mathematical relationship between the vapor pressure and the density, or an empirical relationship between the vapor pressure and the density. For example, an ultrasonic sensor can be employed for sensing a speed of propagation of acoustic waves in the liquid or a fluid composition sensor can provide a fluid composition signal, and the density of the cryogenic liquid can be estimated from inputs comprising the speed of propagation of the acoustic waves or the fluid composition signal. The fluid composition sensor can be at least a methane sensor, for example when the fluid is natural gas, and the computer can be programmed to estimate the density based on the percent composition of methane in natural gas. The computer can yet still be further programmed to calculate a second mass of the vapor, and a total fluid mass as the sum of the first mass and the second mass. The computer can be programmed to estimate a fuelling range for a vehicle from the total fluid mass when the fluid is a fuel for combustion in an internal combustion engine of the vehicle. The computer is programmed to calculate the second mass by calculating a second volume occupied by the vapor, estimating a density of the vapor, and estimating the second mass based on the second volume and the density. The fluid composition sensor can provide the fluid composition signal that is representative of the composition of the vapor, and the computer can be further programmed to estimate the vapor density based on the fluid composition signal.

DETAILED DESCRIPTION OF PREFERRED EMBODIMENT(S)

Figure 1:
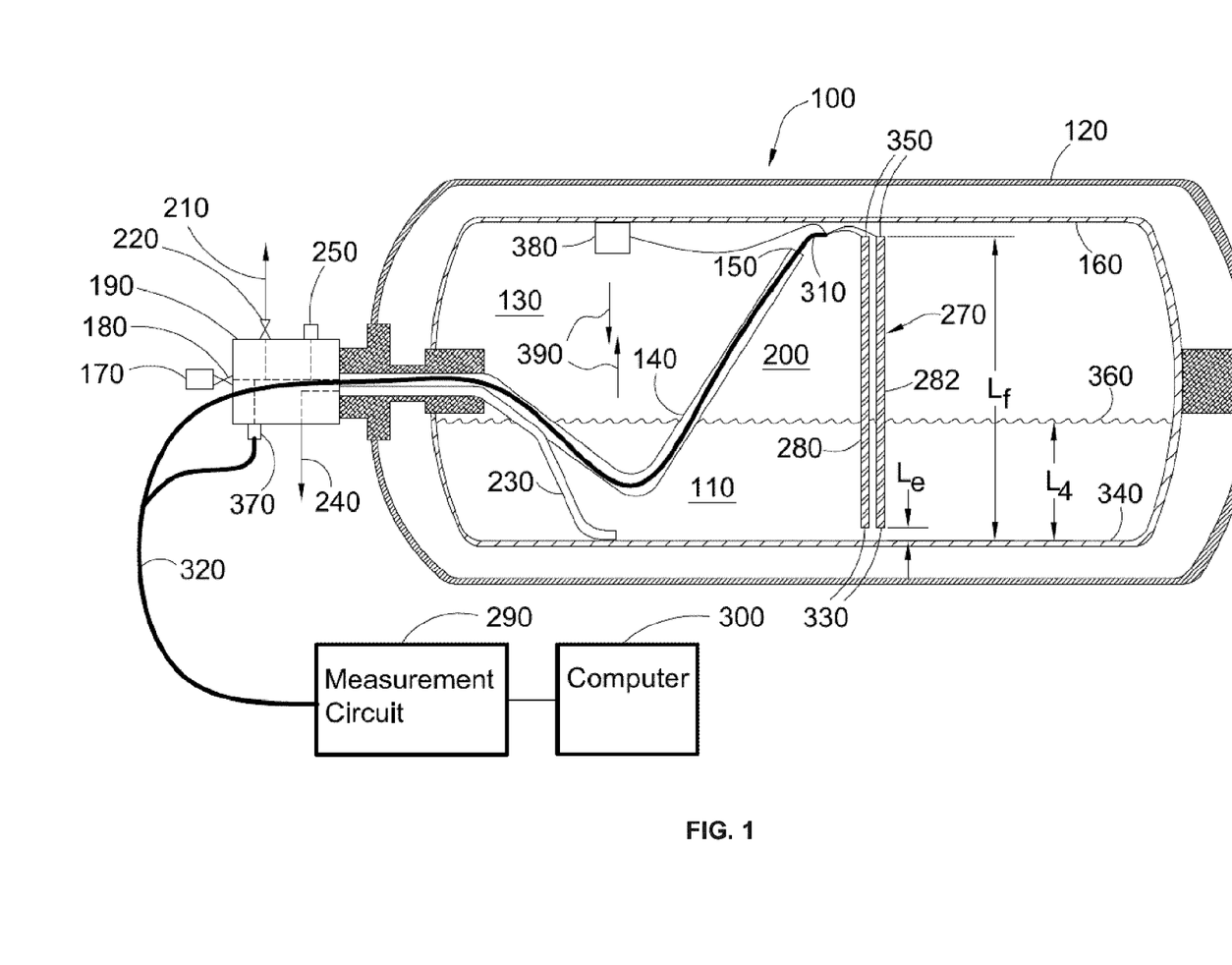
FIG. 1 is a schematic view of a cryogenic storage tank and the apparatus for estimating the fuel volume and mass within the storage tank.

Referring to the figures and first to the illustrated embodiment of FIG. 1, there is shown an apparatus 100 for estimating a volume and a mass of a cryogenic liquid 110 in cryogenic storage tank 120. Cryogenic space 130 is filled by introducing cryogenic fluid through conduit 140 comprising open end 150 disposed near top 160. Cryogenic fluid can be introduced into conduit 140 through coupling 170 which is located outside tank 120. Coupling 170 can comprise shut off valve 180 that opens when coupled to a fill nozzle, and closes when the fill nozzle is not coupled to coupling 170.

Manifold block 190 can be used to reduce the number of fittings and connections to simplify assembly and reduce the number of potential leak points. Internal passages within manifold block 190 connect the conduits that extend into the interior of tank 120 with at least four outside connections. As previously indicated, one internal passage leads from conduit 140 to coupling 170 for filling cryogenic space 130 with cryogenic fluid. Shut off valve 180 need not be integral to coupling 170 and instead can be a separate component installed between manifold block 190 and coupling 170, or to achieve the same effect with less connections, the valve assembly for shut off valve 180 can be installed into a bore made in manifold block 190, whereby manifold block 190 then serves as the body for shut off valve 180.

Cryogenic storage tanks normally build pressure inside cryogenic space 130 during normal use, and before refilling. Vapor is vented from the storage tank to reduce the vapor pressure. With the illustrated embodiment, vapor 200 can be vented from cryogenic space 130 through conduit 140 prior to refilling when a fill nozzle is connected to coupling 170. This is different from conventional systems, which commonly vent vapor 200 to atmosphere, resulting in the gas being wasted and released into the environment. With the illustrated arrangement, vapor 200 that is vented through coupling 170 can be used to pre-cool the hose and/or piping that is used to deliver cryogenic liquid 110 to cryogenic space 130, and this vented vapor can be re-condensed by the filling station and thereby recovered.

A second internal passage within manifold block 190 can be employed to direct vented vapor from conduit 140 to conduit 210. Pressure relief valve 220 can be installed in manifold block 190 or on conduit 210 downstream from manifold block 190. If the filling station is unable to accept vapor 200 that is vented from cryogenic space 130, this feature allows vapor 200 to be vented through conduit 210. As required by regulations governing storage tanks for liquefied gases, to prevent over-pressurization of cryogenic space 130, when the storage tank is in normal operation away from the filling station, pressure relief valve 220 automatically opens when vapor pressure inside cryogenic space 130 exceeds a predetermined set point to vent vapor through conduit 210.

A third internal passage connects outlet conduit 230 with delivery conduit 240, through which cryogenic fluid is deliverable to an end user. As an example, conduits 230 and 240 can supply a low pressure fuelling system with natural gas for a spark ignited engine. In other embodiments, a high pressure pump (not shown) can be employed to deliver gas to an end user at higher pressures, such as a high pressure direct injection system.

A fourth passage internal to manifold 190 connects conduit 140 to pressure sensor 250. Pressure sensor 250 measures the pressure of vapor 200. As cryogenic liquid 110 boils, the vapor pressure within cryogenic space 130 increases. For example, at atmospheric pressure LNG occupies only 1/600th the volume of natural gas in vapor form. As cryogenic liquid 110 boils, it expands to 600 times its volume, thereby increasing the vapor pressure.

Figure 2A:
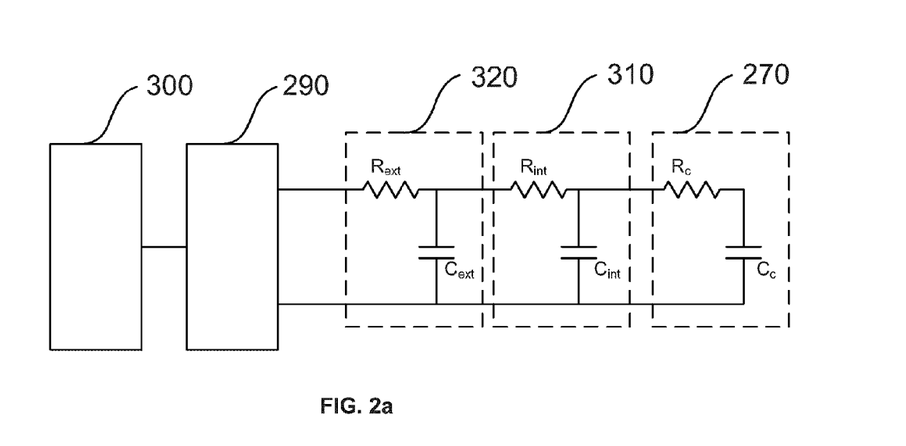
FIGS. 2a and 2b are schematic views of lumped parameter models of external and internal wire harnesses and a level sensor capacitor.

A capacitance-type level sensor comprises a capacitor 270 disposed within cryogenic space 130 for measuring a level of liquid 110. The capacitor 270 comprises a pair of spaced apart conductors 280 and 282. The level sensor further comprises measurement circuit 290 and computer 300. Internal wire harness 310 and external wire harness 320 connect capacitor 270 to measurement circuit 290. With reference to FIG. 2a, there is shown a lumped parameter model of capacitor 270, internal wire harness 310 and external wire harness 320. Capacitor 270 comprises resistance $R_C$ and capacitance $C_C$. Internal wire harness 310 comprises resistance $R_{int}$ and capacitance $C_{int}$. External wire harness 320 comprises resistance $R_{ext}$ and capacitance $C_{ext}$. Note that in other embodiments of the lumped parameter model it is possible to include lumped inductances for capacitor 270 and internal and external wire harnesses 320, however it has been found that at the operational frequencies of measurement circuit 290 the impedances of these inductance are negligible. The resistance $R_C$ represents the finite resistance of conductors 280 and 282. The resistances $R_{int}$ and $R_{ext}$ represent the finite resistance in the wires and connectors of harnesses 310 and 320. Spaced apart conductors form capacitor 270 having capacitance $C_C$. The wires in harnesses 310 and 320 are enclosed in respective cable housings which are routed from measurement circuit 290 to capacitor 270. This arrangement of wires has associated lumped capacitances represented by $C_{int}$ and $C_{ext}$. It has been found that for some applications resistances $R_C$, $R_{int}$ and $R_{ext}$ can be taken as zero and the simplified model of FIG. 2b can be employed.

Capacitance $C_C$ of capacitor 270 can be determined from a voltage across spaced apart conductors 280 and 282 when a measuring signal commanded by computer 300 is applied to charge capacitor 270 via measurement circuit 290 for a specified period of time. Measurement circuit 290 can be similar to that disclosed in Canadian Pat. No. 2,629,960 issued to the present applicant on Dec. 8, 2009 ("the '960 patent"). However, other types of measurement circuits are possible as well.

Figure 2B:
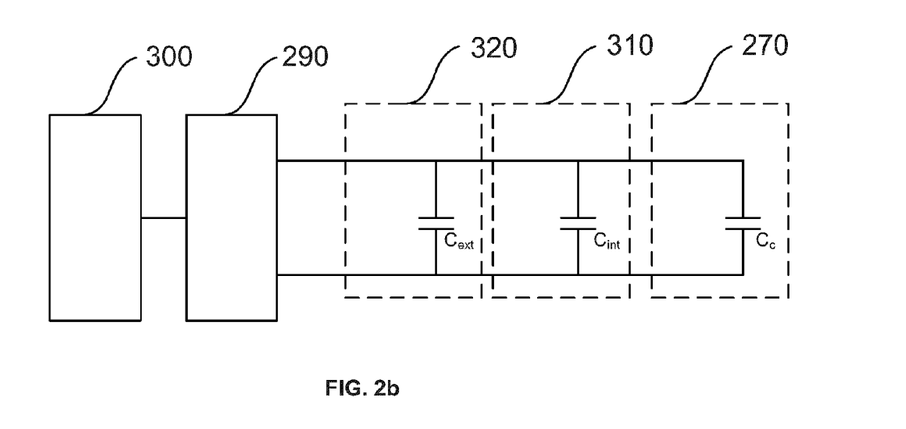
Figure 3:
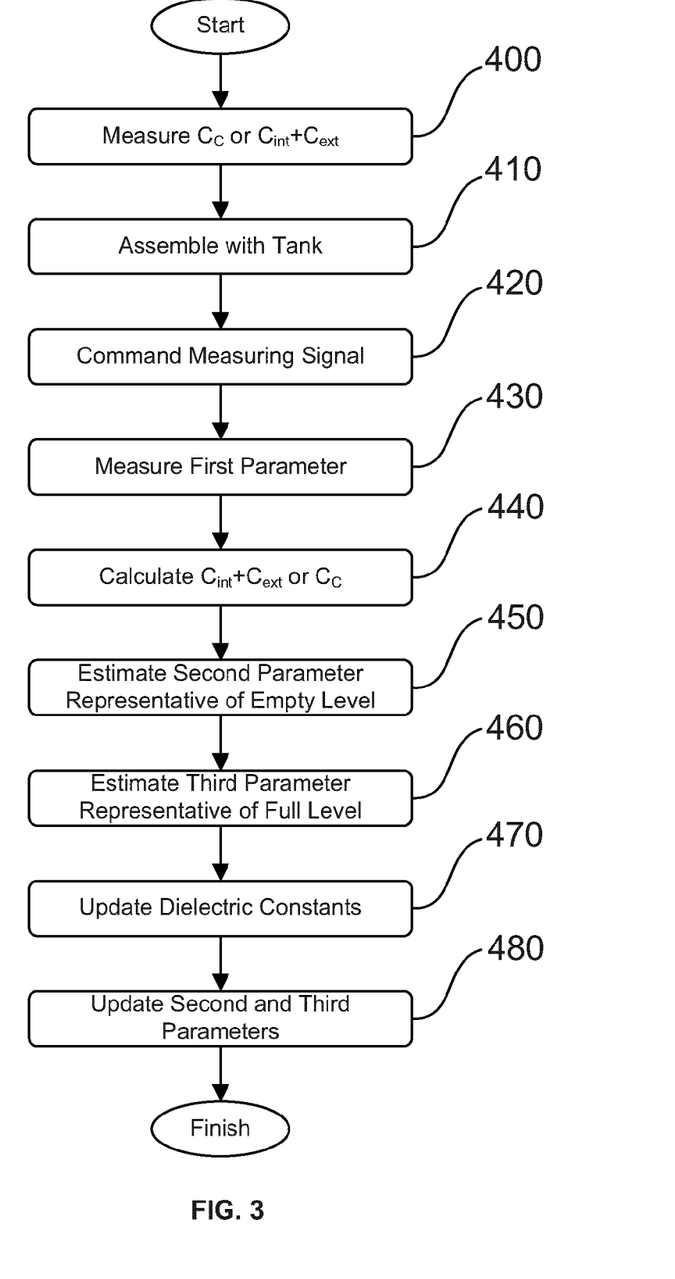
FIG. 3 is a flow chart of a calibration sequence for a capacitance-type level sensor of the apparatus of FIG. 1.

With reference to FIGS. 1 and 3, calibration of the level sensor is now described. The level sensor must be calibrated before it can be employed to measure the level of liquid 110. In the present embodiment, the calibration is described for the model according to FIG. 2b. First, in step 400 either capacitances $C_{int}$ and $C_{ext}$ or capacitance $C_C$ is determined by empirical measurements before installation in tank 120. For example, this can be accomplished with conventional instrumentation that measures capacitance. Preferably, the measurement is conducted once, and the measured value is used for calibration of multiple sensors. In a preferred embodiment, such as when tank 120 is a vehicular fuel tank, capacitance $C_C$ is measured since it has been found that its value is more consistent from level sensor to level sensor. In other embodiments, capacitances $C_{int}$ and $C_{ext}$ can be more consistent in which case their values would be measured. In this example, the measured capacitance represents capacitance $C_{C(dry)}$ when capacitor 270 is in a dry state when only air is between conductors 280 and 282. Next, in step 410 capacitor 270 and wire harnesses 310 and 320 are assembled with tank 120 and computer 300 is programmed with dry capacitance $C_{C(dry)}$ and other parameters as will be described below. Calibration is performed in a dry state when only air is within cryogenic space 130 and between spaced apart conductors 280 and 282. For example, calibration is carried out during manufacturing of storage tank 120 before cryogenic liquid 110 is added to space 130. In step 420, computer 300 commands the measuring signal to be applied to capacitor 270. In step 430, measurement circuit 290 measures total capacitance $C_{T(dry)}$ equal to the total capacitance of wire harnesses 310 and 320 and capacitor 270 and communicates this value to computer 300. In this situation, tank 120 is in the dry state, and total capacitance $C_{T(dry)}$ is a first parameter representative of dry capacitance $C_{C(dry)}$ of the level sensor. Air is a first dielectric for capacitor 270 and has a first dielectric constant $k_{air}$ of approximately 1.00059 at room temperature (25° C.).

The first parameter can be a voltage or a capacitance value, and in the present embodiment the calibration is described for when it is a capacitance. In step 440, computer 300 calculates capacitances $C_{int}$ and $C_{ext}$ according to Eq. 1 below, which follows from the model of FIG. 2b. Capacitances $C_{int}$ and $C_{ext}$ are stored in a memory, for example an EEPROM or FLASH memory, of computer 300.

$$C_{int} + C_{ext} = C_{T(dry)} - C_{C(dry)} \qquad \text{Eq.1}$$

Computer 300 next estimates a second parameter representative of an empty level of cryogenic liquid 110 in tank 120 in step 450. The empty level occurs when only vapor 200 is between spaced apart conductors 280 and 282. In this situation vapor 200 is a second dielectric having a second dielectric constant $k_{vapor}$. The second parameter is the total capacitance $C_{T(empty)}$ and is estimated according to Eqs. 2 and 3 below based upon the first parameter and a first ratio of dielectric constants comprising the first dielectric constant $k_{air}$ and the second dielectric constant $k_{vapor}$. With reference to Eq. 3, $C_{C(dry)}$ was measured in step 400, $C_{int}$ and $C_{ext}$ were determined in step 440, and dielectric constants $k_{air}$ and $k_{vapor}$ are known and were programmed into computer 300 prior to this calibration step.

$$C_{T(empty)} = C_{C(empty)} + C_{int} + C_{ext} \qquad \text{Eq. 2}$$

$$C_{T(empty)} = C_{C(dry)} \frac{k_{vapor}}{k_{air}} + C_{int} + C_{ext} \qquad \text{Eq. 3}$$

It is possible that tank 120 may contain cryogenic liquid 110 at the empty level. For example, lower ends 330 of spaced apart conductors 280 and 282 cannot touch bottom 340 of tank 120 and so an amount of cryogenic liquid 110 that resides at bottom 340 and does not contact the conductors will not be measurable. As the level of cryogenic liquid 110 decreases and falls below the level of lower ends 330 the level 10 sensor will indicate an empty level. Computer 300 is configured during calibration to store the empty level $L_e$, which is the distance lower ends 330 are from bottom 340, and the total capacitance $C_{T(empty)}$ in the empty state, namely, the second parameter, in the memory of computer 300, and to associate $L_e$ with $C_{T(empty)}$.

Next, in step 460, computer 300 estimates a third parameter representative of a full level in tank 120. The full level occurs when only cryogenic liquid 110 is between spaced apart conductors 280 and 282. In this situation cryogenic liquid 110 is a third dielectric having a third dielectric constant $k_{liquid}$. The third parameter is the total capacitance $C_{T(full)}$ and is estimated according to Eqs. 4 and 5 below based upon the first parameter and a second ratio of dielectric constants comprising the first dielectric constant $k_{air}$ and the third dielectric constant $k_{liquid}$. With reference to Eq. 5, $C_{C(dry)}$ was measured in step 400, $C_{int}$ and $C_{ext}$ were determined in step 440, and dielectric constants $k_{air}$ and $k_{liquid}$ are known and were programmed into computer 300 prior to this calibration step.

$$C_{T(full)} = C_{C(full)} + C_{int} + C_{ext} \qquad \text{Eq. 4}$$

$$C_{T(full)} = C_{C(dry)} \frac{k_{liquid}}{k_{air}} + C_{int} + C_{ext} \qquad \text{Eq. 5}$$

It is possible that tank 120 may contain vapor 200 at the full level. For example, upper ends 350 of spaced apart conductors 280 and 282 are spaced below top 160 of tank 120. As the level of cryogenic liquid 110 increases and rises above upper ends 350 the level sensor will indicate a full level. Computer 300 is configured during calibration to store the full level $L_f$, which is the distance upper ends 350 are from bottom 340, and the total capacitance $C_{T(full)}$ in the full state, namely, the third parameter, in the memory of computer 300, and to associate $L_f$ with $C_{T(full)}$. This completes the initial calibration of the level sensor.

In other embodiments, for increased accuracy the model of FIG. 2a can be employed. In this situation, the previously discussed calibration steps would be adjusted to take into consideration the finite resistances $R_{int}$, $R_{ext}$ and $R_C$. For example, resistance $R_C$ would be additionally measured in step 400, measurement circuit 290 would provide computer 300 with conventional total impedance measurements, and Eqs. 1-6 would be adjusted to take into additional consideration the finite resistances $R_{int}$, $R_{ext}$ and $R_C$. For further improved accuracy, the effects of vapor 200 on capacitance $C_{int}$ of internal wire harness 310 can be included in Eqs. 2-5. In this situation, $C_{int}$ needs to be determined independently from Cext, for example $C_{int(dry)}$ can also be measured in step 400, separately from capacitance $C_{C(dry)}$).

The level sensor can be recalibrated during normal operation for improved accuracy according to the following steps. Computer 300 receives a pressure signal from pressure sensor 250 that is representative of the vapor pressure inside cryogenic tank 120. In step 470, computer 300 periodically updates the values of second dielectric constant $k_{vapor}$ and third dielectric constant $k_{liquid}$ as a function of the pressure signal. In step 480, computer 300 can periodically correct the second parameter, which is the total capacitance $C_{T(empty)}$ representative of the empty level $L_e$, based on updated second dielectric constant $k_{vapor}$. Similarly, the third parameter, which is the total capacitance $C_{T(full)}$ representative of the full level $L_f$, can be periodically corrected based on updated third dielectric constant $k_{liquid}$. These updated values can be stored in the memory of computer 300 and used for level measurement as described herein.

Figure 4:
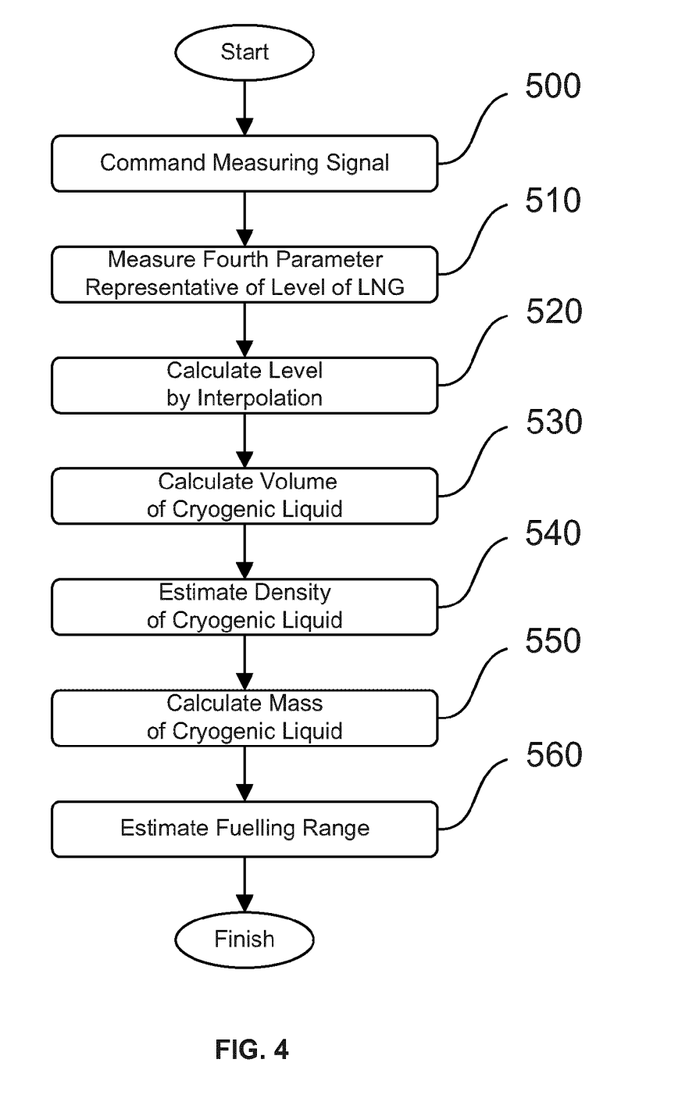
FIG. 4 is a flow chart for the method of estimating the fuel volume and mass of a cryogenic liquid within the storage tank of the apparatus of FIG. 1.
Figure 5:
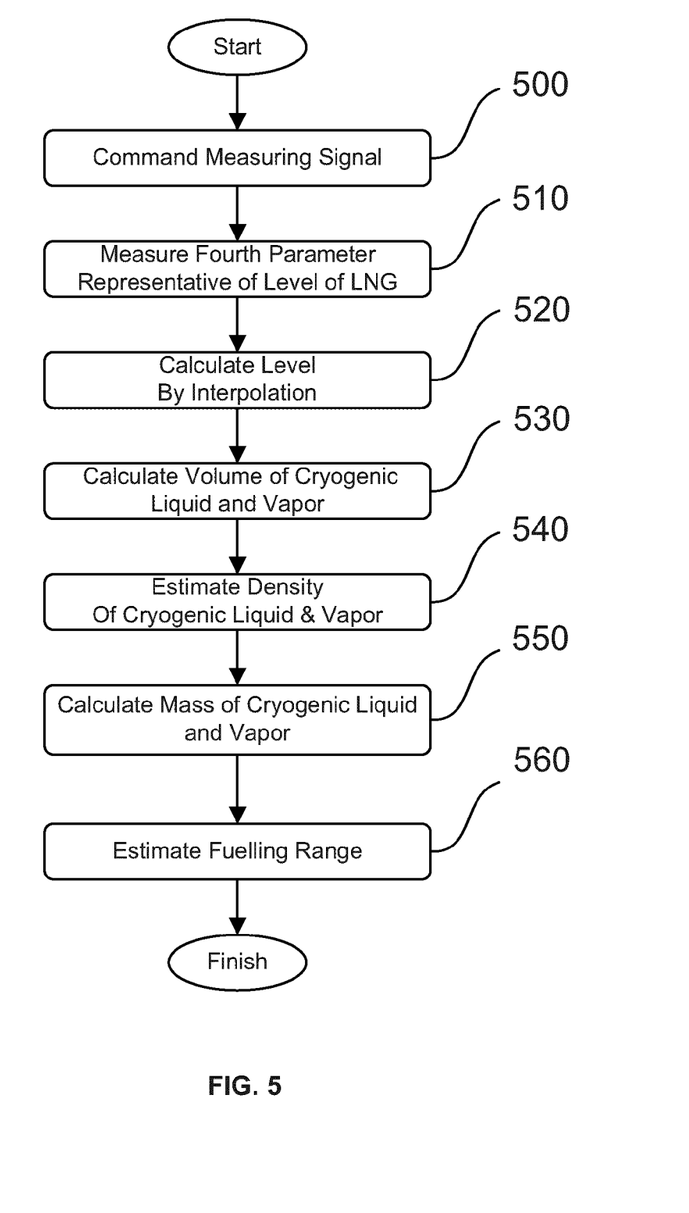
FIG. 5 is a flow chart for the method of estimating the fuel volume and mass of a cryogenic liquid and a vapor within the storage tank of the apparatus of FIG. 1.

With reference to FIGS. 1 and 4, the method of estimating the fuel volume and mass of cryogenic liquid 110 is now described. In step 500, computer 300 commands the measuring signal to be applied to capacitor 270 to determine an unknown level $L_4$ of cryogenic liquid 110 in tank 120. In step 510, measurement circuit 290 measures a fourth parameter as total capacitance $C_{T(L_4)}$ representative of level $L_4$. Computer 300 receives the fourth parameter from measurement circuit 290.

In step 520, computer 300 determines level $L_4$ by first relating the fourth parameter to the second and third parameters, for example by calculating a normalized percentage of the total capacitance $C_{T(L_4)}$ with respect to the total capacitances $C_{T(empty)}$ and $C_{T(full)}$ according to Eq. 6. Level $L_4$ can then be determined by interpolating between the empty level Le and the full level $L_f$ according to Eq. 7.

$$\% \ C_{T(L_4)} = \frac{C_{T(L_4)} - C_{T(empty)}}{C_{T(full)} - C_{T(empty)}} \times 100 \qquad \text{Eq. 6}$$

$$L_4 = L_e + \frac{\% \ C_{T(L_4)}}{100} \times (L_f - L_e) \qquad \text{Eq. 7}$$

In step 530, the volume of cryogenic liquid 110 corresponding to level $L_4$ just determined is estimated by either a mathematical or empirical relationship. For some tanks 120, a formula defining the volume of cryogenic liquid 110 as a function of the level of the cryogenic liquid can be determined. For other tanks, an equation defining such a relationship is more difficult to determine and it is more convenient to empirically relate the volume with the level by performing experiments. In either situation, a look-up table or map can be employed to relate the level to the volume.

The density of cryogenic liquid 110 is determined in step 540. Computer 300 calculates the density of cryogenic liquid 110 based on the vapor pressure signal received from pressure sensor 250. It is noted that cryogenic liquid 110 and vapor 200 are substantially in a state of thermal equilibrium at the boiling temperature of cryogenic liquid 110 and therefore the temperature of cryogenic liquid 110 and vapor 200 is known implicitly based on the vapor pressure. As an example, when cryogenic liquid 110 is LNG, it boils at approximately −162° C. at atmospheric pressure. When tank 120 is in the dry state and filled for the first time, the vapor pressure is substantially equivalent to atmospheric pressure, but as heat gets absorbed by the cold liquid 110 from the surrounding walls in tank 120, it causes increased vaporization. As cryogenic liquid 110 boils and the vapor pressure increases, the boiling temperature increases. The relationship between pressure and boiling temperature is well known and can be employed to determine the temperature. A temperature sensor is not required to determine the temperature.

There are several known methods for predicting the density of cryogenic liquid 110 based on pressure and temperature. These methods include but are not limited to generalized charts, correlations, and equations of state. The generalized charts can be determined, for example, from empirical methods.

In still further embodiments, the density of cryogenic liquid 110 can further be determined as a function of fluid composition of cryogenic liquid 110. For example, when cryogenic liquid 110 is LNG then both the LNG and vapor 200 comprise multiple hydrocarbons, mainly methane, but also ethane, propane, butane and other constituents. Natural gas sold in the market comes in various levels of fuel quality having different compositions of hydrocarbons.

In order to make a determination of the fluid composition, a fifth passage internal to manifold 190 connects conduit 140 to fluid composition sensor 370. Fluid composition sensor 370 is responsive to vapor 200 and liquid 110 to provide a fluid composition signal to computer 300 representative of at least a portion of the composition of vapor 200 and liquid 110. That is, fluid composition sensor 370 can measure the presence of at least one hydrocarbon in conduit 140. For example, fluid composition sensor 370 can be a methane sensor that measures the percentage by volume of methane in vapor 200. Fluid composition sensor 370 can employ a spectroscopy type sensor, but other sensor types are possible. In other examples there can be a plurality of fluid composition sensors 370 each of which can measure the presence of a particular hydrocarbon. By knowing at least the percentage volume of methane in cryogenic liquid 110 and vapor 200, a more accurate determination of the density of cryogenic liquid 110 can be made.

In yet still further embodiments, the density of cryogenic liquid 110 can further be determined as a function of a speed of propagation of acoustic waves travelling through cryogenic liquid 110, for example from ultrasonic sensor 380. Ultrasonic sensor 380 emits high frequency acoustic waves 390 that are reflected from tank bottom 340. The density of liquid 110 can be estimated based on the speed of propagation of waves 390 as determined by round trip travel time and a distance between ultrasonic sensor 380 and tank bottom 340. In other embodiments, ultrasonic sensor 380 can be an ultrasonic level sensor that can also determine the level of liquid 110 in tank 120. In FIG. 1, ultrasonic sensor 380 is connected with internal wiring harness 310 which connects with measurement circuit 290. In other embodiments, ultrasonic sensor 380 can connect directly with computer 300.

In step 550, computer 300 estimates the mass of cryogenic liquid 110 based on inputs comprising the density and the volume of cryogenic liquid 110 determined in steps 540 and 550, respectively. In the present embodiment, cryogenic liquid 110 is employed to power the vehicle. In step 560, an estimate of fuelling range based on a current operating load of the vehicle can be made by knowing the mass of cryogenic liquid 110. For example, at the current operating load of the vehicle the engine speed is known and the quantity of fuel injected per engine cycle is also known. The range of the vehicle at the current operating load can then be determined.

Referring now to FIGS. 1 and 4, another embodiment of the disclosed method is presented wherein like parts to the previous embodiment have like reference numerals. This embodiment is similar to the embodiment of FIG. 3 and like parts are not described in detail, if at all. In some applications both cryogenic liquid 110 and vapor 200 provide fuel to power the vehicle. In this situation vapor 200 can be included in estimations of fuelling range.

In step 540, the volume of cryogenic liquid 110 is determined as in the previous embodiment. Computer 300 additionally calculates a volume of vapor 200 by subtracting the volume of cryogenic liquid 110 from a total volume of cryogenic space 130, which is a known value that is stored in the memory of computer 300.

In step 550, the density of cryogenic liquid 110 is determined as in the previous embodiment. Computer 300 additionally calculates a density of vapor 200 by employing the ideal gas law:

$$\rho = \frac{P}{R_{specific}T}$$

where
ρ is density
P is vapor pressure
T is temperature
$R_{specific}$ the specific gas constant Temperature T is known due to the state of thermal equilibrium between cryogenic liquid 110 and vapor 200, and vapor pressure P.

Computer 300 calculates the mass of cryogenic liquid 110 in step 560 as in the previous embodiment. Additionally, computer 300 calculates the mass of vapor 200 from inputs comprising the volume of vapor 200 and the density of vapor 200. In step 570, computer 300 estimates the fuelling range of the vehicle based on the mass of cryogenic liquid 110 and vapor 200. When all liquid 110 is consumed by the vehicle, computer 300 can calculate how much remaining vapor 200 can be consumed for fuelling based on a minimum required gaseous fuel pressure.

While particular elements, embodiments and applications of the present invention have been shown and described, it will be understood, that the invention is not limited thereto since modifications can be made by those skilled in the art without departing from the scope of the present disclosure, particularly in light of the foregoing teachings.

What is claimed is:

1. A method of estimating fluid mass in a cryogenic tank that holds a multiphase fluid comprising a liquid and a vapour, wherein the liquid has a density and the vapour has a pressure, the method comprising steps of:
    employing a capacitance-type level sensor to provide a parameter representative of a level of the liquid in the cryogenic tank;
    measuring the vapour pressure inside the cryogenic tank;
    adjusting respective parameters representative of a capacitance of an empty level and a capacitance of a full level of the capacitance-type level sensor as a function of the vapour pressure;
    measuring a parameter representative of the actual capacitance of the capacitance-type level sensor;
    calculating the level of the liquid in the cryogenic tank as a function of the parameters representative of the capacitance of the empty level, the capacitance of the full level, and the actual capacitance of the capacitance-type level sensor;
    calculating a first volume of the liquid as a function of the level of the liquid in the cryogenic tank; and
    calculating a first mass of the liquid from inputs comprising the first volume and the density of the liquid.

2. The method of claim 1, wherein the fluid is a fuel for combustion in an internal combustion engine in a vehicle, the method further comprising a step of estimating a fuelling range for the vehicle from the first mass.

3. The method of claim 1, wherein the step of employing the capacitance-type level sensor comprises sub-steps of:
    providing a pair of spaced apart conductors, the spaced apart conductors being disposed within the cryogenic tank and forming in part a capacitor; and
    calibrating the capacitance-type level sensor at least once prior to first introduction of the cryogenic liquid in the cryogenic tank, wherein calibrating the capacitance-type level sensor comprises steps of:
        applying a measuring signal to the capacitor;
        measuring a parameter representative of a dry capacitance of the capacitor in a dry state, a first dielectric having a first dielectric constant being disposed between the spaced apart conductors in the dry state;
        estimating the parameter representative of the capacitance of the empty level in the cryogenic tank, a second dielectric having a second dielectric constant being disposed between the spaced apart conductors at the empty level, the parameter representative of the capacitance of the empty level being estimated based on the parameter representative of the dry capacitance and a first ratio of dielectric constants comprising the first dielectric constant and the second dielectric constant; and
        estimating the parameter representative of the capacitance of the full level in the cryogenic tank, a third dielectric having a third dielectric constant being disposed between the spaced apart conductors at the full level, the parameter representative of the capacitance of the full level being estimated based on the parameter representative of the dry capacitance and a second ratio of dielectric constants comprising the first dielectric constant and the third dielectric constant.

4. The method of claim 3, wherein the second dielectric is the vapour and the third dielectric is the liquid.

5. The method of claim 3, wherein the step of calibrating further comprises a sub-step of calculating the second dielectric constant and the third dielectric constant as a function of the vapour pressure.

6. The method of claim 1, wherein the step of calculating the level of the liquid in the cryogenic tank comprises a sub-step of interpolating the level of the liquid in the cryogenic tank between the empty level and the full level based on the actual capacitance of the capacitance-type level sensor.

7. The method of claim 1, wherein the step of calculating the first volume comprises a sub-step of employing a mathematical relationship between the level of the liquid in the cryogenic tank and the first volume.

8. The method of claim 1, wherein the step of calculating the first volume comprises a sub-step of employing an empirical relationship between the level of the liquid in the cryogenic tank and the first volume.

9. The method of claim 1, wherein the step of calculating the first mass comprises
    estimating the density of the liquid from inputs comprising the vapour pressure.

10. The method of claim 9, wherein the step of estimating the density comprises a sub-step of employing a mathematical relationship between the vapour pressure and the density.

11. The method of claim 9, wherein the step of estimating the density comprises a sub-step of employing an empirical relationship between the vapour pressure and the density.

12. The method of claim 9, wherein the density is estimated from inputs comprising a speed of propagation of acoustic waves through the liquid.

13. The method of claim 9, wherein the step of estimating the density comprises sub-steps of:
    (i) estimating a composition of the liquid; and
    (ii) estimating the density based on the composition of the liquid.

14. The method of claim 1, wherein the step of calculating the first mass comprises a sub-step of estimating a composition of the liquid.

15. The method of claim 14, wherein the step of estimating the composition comprises a sub-step of employing a fluid composition sensor.

16. The method of claim 14, wherein the step of estimating the composition comprises a sub-step of estimating a methane composition.

17. The method of claim 1, further comprising a step of calculating a second mass of the vapour, a total fluid mass being the sum of the first mass and the second mass.

18. The method of claim 17, wherein the fluid is a fuel for combustion in an internal combustion engine of a vehicle, the method further comprising a step of estimating fuelling range for the vehicle from the total fluid mass.

19. The method of claim 17, wherein the step of calculating the second mass comprises sub-steps of:
   (i) calculating a second volume occupied by the vapour;
   (ii) estimating a density of the vapour; and
   (iii) estimating the second mass based on the second volume and the density.

20. The method of claim 19, wherein the step of estimating the density comprises a sub-step of calculating the density as a function of the vapour pressure.

21. The method of claim 19, wherein the step of estimating the density comprises sub-steps of:
   (i) estimating a composition of the vapour; and
   (ii) estimating the density based on the composition of the vapour.

22. The method of claim 1, wherein the fluid is natural gas.

23. An apparatus for estimating fluid mass in a cryogenic tank that holds a multiphase fluid comprising a liquid and a vapour, the apparatus comprising:
   a capacitance-type level sensor capable of providing a parameter representative of a capacitance of the capacitance-type level sensor;
   a pressure sensor capable of providing a pressure signal representative of vapour pressure inside the cryogenic tank; and
   a computer operatively connected with the capacitance-type level sensor and the pressure sensor to receive the parameter and the pressure signal, and being programmed to:
      determine vapour pressure inside the tank as a function of the pressure signal;
      adjust respective parameters representative of a capacitance of an empty level and a capacitance of a full level of the capacitance-type level sensor as a function of the vapour pressure;
      calculate a level of the liquid in the cryogenic tank as a function of the parameters representative of the empty level capacitance, the full level capacitance and the capacitance of the capacitance-type level sensor;
      calculate a first volume of the liquid as a function of the level of the liquid in the cryogenic tank; and
      calculate a first mass of the liquid from inputs comprising the first volume and a density of the liquid.

24. The apparatus of claim 23, wherein the fluid is natural gas.

25. The apparatus of claim 23, wherein the fluid is a fuel for combustion in an internal combustion engine in a vehicle, the computer being further programmed to estimate a fuelling range for the vehicle from the first mass.

26. The apparatus of claim 23, wherein the capacitance-type level sensor comprises a pair of spaced apart conductors disposed within the cryogenic tank and a measurement apparatus operatively connected with the spaced apart conductors and being adapted to apply a measuring signal thereto and measure instantaneous values of parameters therefrom representative of corresponding instantaneous values of capacitance of the spaced apart conductors, the computer being in communication with the measurement apparatus and being further programmed to calibrate the capacitance-type level sensor at least once prior to first introduction of the cryogenic liquid in the cryogenic tank, the computer being programmed to:
   command the measuring signal be applied to the spaced apart conductors;
   receive a parameter from the measurement apparatus representative of a dry capacitance of the spaced apart conductors in a dry state, a first dielectric having a first dielectric constant being disposed between the spaced apart conductors in the dry state;
   estimate the parameter representative of the capacitance of the empty level in the cryogenic tank, a second dielectric having a second dielectric constant being disposed between the spaced apart conductors at the empty level, the parameter representative of the capacitance of the empty level being estimated based on the parameter representative of the dry capacitance and a first ratio of dielectric constants comprising the first dielectric constant and the second dielectric constant; and
   estimate the parameter representative of the capacitance of the full level in the cryogenic tank, a third dielectric having a third dielectric constant being disposed between the spaced apart conductors at the full level, the parameter representative of the capacitance of the full level being estimated based on the parameter representative of the dry capacitance and a second ratio of dielectric constants comprising the first dielectric constant and the third dielectric constant.

27. The method of claim 26, wherein the second dielectric is the vapour and the third dielectric is the liquid.

28. The apparatus of claim 26, wherein the computer is further programmed to calculate the second dielectric constant and the third dielectric constant as a function of the vapour pressure.

29. The apparatus of claim 23, wherein the computer is further programmed to interpolate the level of the liquid in the cryogenic tank between the empty level and the full level based on the capacitance of the capacitance-type level sensor.

30. The apparatus of claim 23, wherein the computer is further programmed to employ a mathematical relationship between the level of the liquid in the cryogenic tank and the first volume.

31. The apparatus of claim 23, wherein the computer is further programmed to employ an empirical relationship between the level of the liquid in the cryogenic tank and the first volume.

32. The apparatus of claim 23, wherein the computer is further programmed to:
   estimate the density of the liquid from inputs comprising the vapour pressure.

33. The apparatus of claim 32, wherein the computer is further programmed to employ a mathematical relationship between the vapour pressure and the density.

34. The apparatus of claim 32, wherein the computer is further programmed to employ an empirical relationship between the vapour pressure and the density.

35. The apparatus of claim 32, wherein the apparatus further comprises an ultrasonic sensor for sensing a speed of propagation of acoustic waves in the liquid, the density of the cryogenic liquid being estimated from inputs comprising the speed of propagation of the acoustic waves.

36. The apparatus of claim 23, wherein the apparatus further comprises a fluid composition sensor providing a fluid composition signal; the computer being responsive to the fluid composition signal to estimate at least a portion of a composition of the liquid.

37. The apparatus of claim 36, wherein the fluid composition sensor is a methane composition sensor.

38. The apparatus of claim 36, wherein the computer is further programmed to estimate the density based on the at least a portion of the composition of the liquid.

39. The apparatus of claim 23, wherein the computer is further programmed to calculate a second mass of the vapour, a total fluid mass being the sum of the first mass and the second mass.

40. The apparatus of claim 39, wherein the fluid is a fuel for combustion in an internal combustion engine of a vehicle, the computer being further programmed to estimate a fuelling range for the vehicle from the total fluid mass.

41. The apparatus of claim 39, wherein the computer is further programmed to:
calculate a second volume occupied by the vapour;
estimate a density of the vapour; and
estimate the second mass based on the second volume and the density.

42. The apparatus of claim 41, wherein the computer is further programmed calculate the density as a function of the vapour pressure.

43. The apparatus of claim 41, wherein the apparatus further comprises a fluid composition sensor providing a fluid composition signal; the computer being responsive to the fluid composition signal to estimate at least a portion of a composition of the vapour, the computer being further programmed to estimate the density based on the at least a portion of the composition of the vapour.

* * * * *